US012594313B2

(12) United States Patent
Park et al.

(10) Patent No.: US 12,594,313 B2
(45) Date of Patent: Apr. 7, 2026

(54) COMPOSITION FOR ALLEVIATING CARDIOVASCULAR DISEASE OR OSTEOPOROSIS, COMPRISING MIXED EXTRACT OF HOP AND CYNANCHUM WILFORDII AS ACTIVE INGREDIENT, AND METHOD FOR TREATING OR ALLEVIATING CARDIOVASCULAR DISEASE OR OSTEOPOROSIS USING SAME

(71) Applicant: LG HOUSEHOLD & HEALTH CARE LTD., Seoul (KR)

(72) Inventors: Dong-Jun Park, Seoul (KR); Eun-Mi Sun, Seoul (KR); Hong-Gu Lee, Seoul (KR); Ho-Song Cho, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 363 days.

(21) Appl. No.: 18/130,765

(22) Filed: Apr. 4, 2023

(65) Prior Publication Data

US 2023/0372422 A1 Nov. 23, 2023

(30) Foreign Application Priority Data

Apr. 4, 2022 (KR) ........................ 10-2022-0041720

(51) Int. Cl.
| | |
|---|---|
| A61K 36/24 | (2006.01) |
| A61K 9/00 | (2006.01) |
| A61K 9/16 | (2006.01) |
| A61K 31/352 | (2006.01) |
| A61K 31/353 | (2006.01) |
| A61K 31/573 | (2006.01) |
| A61K 31/7048 | (2006.01) |
| A61K 36/185 | (2006.01) |
| A61K 36/488 | (2006.01) |
| A61K 36/752 | (2006.01) |
| A61P 3/06 | (2006.01) |
| A61P 9/10 | (2006.01) |
| A61P 9/12 | (2006.01) |
| A61P 19/10 | (2006.01) |

(52) U.S. Cl.
CPC ........... *A61K 36/24* (2013.01); *A61K 9/0056* (2013.01); *A61K 9/1611* (2013.01); *A61K 9/1617* (2013.01); *A61K 9/1623* (2013.01); *A61K 9/1652* (2013.01); *A61K 9/1664* (2013.01); *A61K 31/352* (2013.01); *A61K 31/353* (2013.01); *A61K 31/573* (2013.01); *A61K 31/7048* (2013.01); *A61K 36/3486*

(2024.05); *A61K 36/488* (2013.01); *A61K 36/752* (2013.01); *A61P 3/06* (2018.01); *A61P 9/10* (2018.01); *A61P 9/12* (2018.01); *A61P 19/10* (2018.01)

(58) Field of Classification Search
None
See application file for complete search history.

(56) References Cited

U.S. PATENT DOCUMENTS

| | | | |
|---|---|---|---|
| 5,763,414 A * | 6/1998 | Bok ........................ | A61P 43/00 |
| | | | 514/456 |
| 2005/0032882 A1 | 2/2005 | Chen | |
| 2007/0218155 A1* | 9/2007 | Kuhrts ..................... | A61P 3/06 |
| | | | 424/778 |
| 2021/0401918 A1 | 12/2021 | Lee et al. | |

FOREIGN PATENT DOCUMENTS

| | | |
|---|---|---|
| EP | 1 543 834 A1 | 6/2005 |
| KR | 10-2017-0121532 A | 11/2017 |
| KR | 10-2020-0062036 A | 6/2020 |

OTHER PUBLICATIONS

Kim (Journal of Functional Foods (2019), vol. 59, pp. 281-290).*
Wang et al., "Cynanchum Auriculatum Royle ex Wight., Cynanchum Bungei Decne. and Cynanchum Wilfordii (Maxim.) Hemsl.: Current Research and Prospects," Molecules, vol. 26, No. 23, Nov. 23, 2021, pp. 1-40 (41 pages total).
Chiba et al., "Hesperidin, a Citrus Flavonoid, Inhibits Bone Loss and Decreases Serum and Hepatic Lipids in Ovariectomized Mice," The Journal of Nutrition, vol. 133, 2003, pp. 1892-1897.
Kim et al., "Efficacy and Safety of Kudzu Flower-Mandarin Peel on Hot Flashes and Bone Markers in Women during the Menopausal Transition: A Randomized Controlled Trial," Nutrients, vol. 12, No. 3237, Oct. 22, 2020, pp. 1-13.

* cited by examiner

*Primary Examiner* — Susan Hoffman
(74) *Attorney, Agent, or Firm* — Birch, Stewart, Kolasch & Birch, LLP

(57) ABSTRACT

The present disclosure relates to a composition for treating, preventing or alleviating cardiovascular disease and/or osteoporosis, which contains a mixed extract of hop and *Cynanchum wilfordii* as an active ingredient, and a method for treating or alleviating cardiovascular disease and/or osteoporosis. The composition and method of the present disclosure provide superior effect of alleviating, preventing or treating cardiovascular disease and/or osteoporosis while using a small amount of hop.

5 Claims, No Drawings

1

COMPOSITION FOR ALLEVIATING CARDIOVASCULAR DISEASE OR OSTEOPOROSIS, COMPRISING MIXED EXTRACT OF HOP AND CYNANCHUM WILFORDII AS ACTIVE INGREDIENT, AND METHOD FOR TREATING OR ALLEVIATING CARDIOVASCULAR DISEASE OR OSTEOPOROSIS USING SAME

TECHNICAL FIELD

The present disclosure relates to a composition for alleviating cardiovascular disease or osteoporosis and a method for treating or alleviating cardiovascular disease and/or osteoporosis using the same. More particularly, it relates to a composition for alleviating cardiovascular disease or osteoporosis, which contains a mixed plant extract, a use of the extract, and a method for alleviating or treating cardiovascular disease or osteoporosis using the mixed extract.

BACKGROUND ART

Bone tissue consists of cellular substrates such as collagen and glycoproteins and various types of cells such as osteoblast, osteoclasts, osteocytes, etc. Osteoblasts derived from bone marrow stromal cells play a major role in bone formation.

As a representative example of bone diseases, osteoporosis is an unavoidable symptom in the elderly, especially postmenopausal women, although the degree varies. Interest in osteoporosis and its therapeutic agents is increasing gradually in developed countries as the population ages. Global research institutes and pharmaceutical companies are investing heavily in the development of therapeutic agents for bone diseases.

So far, several substances have been developed as therapeutic agents for osteoporosis. Estrogen, which has been used the most frequently as a therapeutic agent for osteoporosis among them, has a disadvantage in that its actual efficacy has not been verified yet and it must be taken continuously through life. In addition, long-term administration can cause side effects such as increased risk of breast cancer or uterine cancer. Alrendronate also has problems in that its efficacy is not clear, absorption in the digestive tract is slow, and inflammation of the gastric and esophageal mucosa is caused. Calcium supplements are known to be highly effective with few side effects, but they are for prevention rather than treatment. In addition, vitamin D preparations such as calcitonin are known, but researches on their efficacy and side effects have not yet been conducted enough.

Cardiovascular disease is a collective term for diseases of the circulatory system such as the heart, blood vessels, etc. It includes hypertension, coronary artery disease, angina, myocardial infarction, atherosclerosis (arteriosclerosis), arrhythmia, stroke, etc. In the past, it was known that decrease in female hormones was related with the development of arteriosclerosis. Formerly, taking female hormones was recommended for the purpose of preventing arteriosclerosis, but recent studies have shown that taking female hormones during menopause did not reduce the incidence of heart disease and did not delay the progression of the heart disease in patients having the disease. Rather, it has been suggested that it may increase the risk of heart disease. Therefore, it can be said that the materials used in hormone therapy are not necessarily effective in treating or alleviating cardiovascular diseases.

Hop is known to contain 8-prenylnaringenin, which exhibits potent phytoestrogenic activity. Hop is known to be helpful in alleviating various menopausal symptoms such as hot flushes, osteoporosis, etc. helpful for digestive disorders such as indigestion, constipation, bloating, etc. and helpful in relieving mental problems such as insomnia, stress, anxiety, etc. It is used in hormone replacement therapy for menopausal disorders. However, it use has been limited due to its bitter taste and side effects that may occur in case of excessive intake.

Accordingly, researches are being conducted to find a substance that can be administered safely into the human body with few side effects.

DISCLOSURE

Technical Problem

The present disclosure is designed to solve the problems of the related art, and therefore the present disclosure is directed to providing a new composition, specifically a food or pharmaceutical composition, for treating, preventing or alleviating cardiovascular disease and/or osteoporosis. The present disclosure is also directed to providing a novel use of a mixed extract for treating, preventing or alleviating cardiovascular disease and/or osteoporosis, or a method for treating or alleviating cardiovascular disease and/or osteoporosis.

Technical Solution

In an exemplary embodiment, the present disclosure provides a food composition for alleviating cardiovascular disease and/or osteoporosis, which contains a mixed extract of hop and *Cynanchum wilfordii* as an active ingredient. The composition contains 8-prenylnaringenin and caudatin, and the composition contains 0.1-5 mg/g of 8-prenylnaringenin and 0.05-1.5 mg/g of caudatin.

The mixed extract of hop and *Cynanchum wilfordii* may be contained in an amount effective for alleviating or treating cardiovascular disease and/or osteoporosis. For example, when the composition is formulated into a food, a medicine, etc., it may contain about 30-600 mg, about 30-550 mg, about 30-500 mg, about 30-450 mg, about 30-400 mg, about 30-350, about 30-300, about 30-250, about 30-200, about 30-150, about 30-120, about 30-100, about 30-60, about 30-50, about 50-600 mg, about 50-550 mg, about 50-500 mg, about 50-450 mg, about 50-400 mg, about 50-350, about 50-300, about 50-250, about 50-200, about 50-150, about 50-120, about 50-100, about 50-60, about 60-600 mg, about 60-550 mg, about 60-500 mg, about 60-450 mg, about 60-400 mg, about 60-350, about 60-300, about 60-250, about 60-200, about 60-150, about 60-120, about 60-100, about 100-600 mg, about 100-550 mg, about 100-500 mg, about 100-450 mg, about 100-400 mg, about 100-350, about 100-300, about 100-250, about 100-200, about 100-150, about 100-120, about 120-600 mg, about 120-550 mg, about 120-500 mg, about 120-450 mg, about 120-400 mg, about 120-350, about 120-300, about 120-250, about 120-200, about 120-150, about 150-600 mg, about 150-550 mg, about 150-500 mg, about 150-450 mg, about 150-400 mg, about 150-350, about 150-300, about 150-250, about 150-200, about 200-600 mg, about 200-550 mg, about 200-500 mg, about 200-450 mg, about 200-400 mg, about 200-350, about 200-300, about 200-250, about 250-600 mg, about 250-550 mg, about 250-500 mg, about 250-450 mg, about 250-400 mg, about 250-350, about 250-300, about 300-600 mg, about 300-550 mg, about 300-500 mg, about 300-450 mg, about 300-400 mg, about 300-350, about 350-600 mg, about 350-550 mg, about 350-500 mg, about 350-450 mg, about 350-400 mg, about 400-600 mg, about 400-550 mg, about 400-500 mg, about 400-450 mg, about 450-600 mg, about 450-550 mg, about 450-500 mg, about 500-600 mg, about 500-550 mg or about 550-600 mg, e.g., about 100 mg, about 120 mg, about 150 mg, about 180 mg, about 200 mg, about 240 mg, about 250 mg, about 300 mg, about 350 mg, about 360 mg, about 400 mg, about 420 mg or 600 mg of the mixed extract. The above amounts may be understood as daily, weekly or monthly doses, and may be understood as the amounts administered at once. The expression 'about' used herein may be understood as an error range of ±10% of the corresponding values. For example, about 100 mg may be understood as 90-110 mg. The mixed extract may be a mixture of a hop extract and a *Cynanchum wilfordii* extract at a weight ratio of 1:0.1-10. The mixed extract provides a food composition for improving cardiovascular diseases and/or osteoporosis, characterized in that a mixture of a hop extract and a *Cynanchum wilfordii* extract in a weight ratio of 1:0.1-10.

In an exemplary embodiment of the present disclosure, the composition may contain 0.005-30 wt %, 0.01-28 wt %, 0.05-25 wt %, 0.1-23 wt %, 0.5-22 wt %, 1-20 wt %, 5-18 wt % or 8-15 wt % of a hop extract based on the total weight of the composition, and may contain 0.005-50 wt %, 0.01-45 wt %, 0.05-40 wt %, 0.5-38 wt %, 1-35 wt %, 5-33 wt %, 10-32 wt %, 15-31 wt % or 20-30 wt % of a *Cynanchum wilfordii* extract based on the total weight of the composition. The above content ranges may be advantageous for achieving the purpose of the present disclosure.

The cardiovascular disease may include one or more selected from a group consisting of hypertension, coronary artery disease, angina, myocardial infarction, stroke and arrhythmia.

The composition may have the ability of reducing blood cholesterol concentration or inhibiting osteoclast differentiation.

In another exemplary embodiment, the present disclosure provides a pharmaceutical composition for treating or alleviating cardiovascular disease and/or osteoporosis, which contains a mixed extract of hop and *Cynanchum wilfordii* as an active ingredient. The composition contains 8-prenylnaringenin and caudatin, and the composition contains 0.1-5 mg/g of 8-prenylnaringenin and 0.05-1.5 mg/g of caudatin.

The present disclosure provides a pharmaceutical composition for treating or alleviating cardiovascular disease and/or osteoporosis, wherein the mixed extract is a mixture of a hop extract and a *Cynanchum wilfordii* extract at a weight ratio of 1:0.1-10.

In an exemplary embodiment, the present disclosure may provide a pharmaceutical composition for treating or alleviating cardiovascular disease and/or osteoporosis, which contains 8-15 wt % of a hop extract and 20-30 wt % of a *Cynanchum wilfordii* extract based on the total weight of the composition.

The cardiovascular disease may include one or more selected from a group consisting of hypertension, coronary artery disease, angina, myocardial infarction, stroke and arrhythmia.

The pharmaceutical composition may have the ability of reducing blood cholesterol concentration or inhibiting osteoclast differentiation.

In another exemplary embodiment, the present disclosure provides a method for treating or alleviating cardiovascular disease and/or osteoporosis by administering an effective amount of a mixed extract of hop and *Cynanchum wilfordii* to an individual in need of treatment or alleviation of cardiovascular disease and/or osteoporosis.

The mixed extract may be a mixture of a hop extract and a *Cynanchum wilfordii* extract at a weight ratio of 1:0.1-10.

The method may include a step of administering a composition containing the mixed extract, and the composition may contain 8-15 wt % of a hop extract and 20-30 wt % of a *Cynanchum wilfordii* extract based on the total weight of the composition.

The mixed extract may contain 8-prenylnaringenin and hesperidin, and the mixed extract may contain 0.1-8 mg/g of 8-prenylnaringenin and 0.05-1.5 mg/g of caudatin.

The method may provide reduction of blood cholesterol concentration and osteoclast differentiation inhibition.

Advantageous Effects

A composition containing a mixed extract according to the present disclosure is effective in preventing or alleviating cardiovascular disease and/or osteoporosis.

In addition, the mixed extract according to the present disclosure and a composition containing the same are highly useful for treatment of cardiovascular disease and/or osteoporosis.

BEST MODE

In an exemplary embodiment, the present disclosure provides a composition for treating, preventing or alleviating cardiovascular disease and/or osteoporosis, e.g., a food or pharmaceutical composition, which contains a mixed extract of hop and *Cynanchum wilfordii* as an active ingredient. In another exemplary embodiment, the present disclosure provides a use of the mixed extract or the composition for treating, preventing or alleviating cardiovascular disease and/or osteoporosis. In another exemplary embodiment, the present disclosure provides a method for treating, preventing or alleviating cardiovascular disease and/or osteoporosis by administering an effective amount of a mixed extract of a hop extract and a *Cynanchum wilfordii* extract to an individual in need thereof. Specifically, the present disclosure may provide a composition for promoting bone formation and/or improving blood lipids, a use of the composition, and a method for using the composition. In addition, the use of the mixed extract of hop and *Cynanchum wilfordii* can avoid uterine enlargement symptoms, etc. which may occur when a large amount of hop is used to ameliorate the symptoms. Also, preference can be improved by using a smaller amount of hop.

In another exemplary embodiment, the composition may further contain another plant extract. Specifically, it may contain a plant extract such as *Pueraria* flower (specifically *Pueraria thomsonii* flower), etc. within a range not negatively affecting the purpose of the present disclosure.

The mixed extract of hop and *Cynanchum wilfordii* of the present disclosure may exhibit superior effect of alleviating, preventing or treating cardiovascular disease and/or osteoporosis and fewer side effects when hop and *Cynanchum wilfordii* are used together.

Hop (hops, *Humulus lupulus*) is a tendril plant native to Europe, Australia, North America, etc. Various compounds present in a hop extract are known to exhibit various physiological activities including anticancer, antioxidant and skin-whitening effects. Specifically, the mixed extract of the present disclosure may contain an extract obtained from the shoot, flower, bud or fruit of hop, more specifically an extract obtained from the flower or bud of hop. Compounds such as isoxanthohumols, etc. including 8-prenylnaringenin are known as active ingredients in the hop extract. However, hop has the problem in that the administration dose is limited because the uterine weight of mice was increased when it was administered in excess amounts and it has characteristic odor and very strong astringent taste.

*Cynanchum wilfordii* refers to the tuberous root of *Cynanchum wilfordii*. In oriental medicine, the root of *Cynanchum wilfordii* has been used as a medicinal substance, and is known to have nourishing, tonic and blood tonic activities. It tastes bitter, sweet and astringent. In the present disclosure, the *Cynanchum wilfordii* extract refers to the extract of the root of *Cynanchum wilfordii*.

The inventors of the present disclosure have completed the present disclosure by finding out that the mixed extract of hop and *Cynanchum wilfordii* exhibits the effect of inhibiting cholesterol synthesis, increasing NO production for vascular relaxation, promoting osteoblast differentiation and increasing the production of bone tissue components, and thus can exhibit an effect of alleviating, preventing and/or treating cardiovascular disease and/or osteoporosis.

In the present disclosure, the cardiovascular disease may include hypertension, coronary artery disease, angina, myocardial infarction, stroke, arrhythmia, etc., although not being limited thereto.

In the present disclosure, osteoporosis refers to the condition in which the risk of fracture is high due to decreased bone strength, owing to genetic factors, premature menopause, medication, smoking, etc. Menopausal osteoporosis may occur due to decreased hormone production owing to menopause. The menopausal osteoporosis refers to the symptoms of osteoporosis caused by imbalance between osteoblasts involved in bone formation and osteoclasts involved in tissue destruction and resorption owing to decreased hormone production in postmenopausal women.

In the present disclosure, 'prevention' refers to any action of suppressing or delaying the symptoms by administering the mixed extract and/or composition of the present disclosure.

In the present disclosure, 'treatment' refers to any action of ameliorating or eliminating the symptoms by administering the mixed extract and/or composition of the present disclosure.

In the present disclosure, 'alleviation' refers to any action of ameliorating or favorably changing the symptoms by administering the mixed extract and/or composition of the present disclosure as compared to before the administration.

The extract contained in the composition of the present disclosure may be contained in an effective amount. The term 'effective amount' refers to an amount of the extract capable of suppressing or delaying cardiovascular disease and/or osteoporosis, or ameliorating the symptoms that have occurred already. In an exemplary embodiment, it may be understood as the amount administered orally to an individual, which is capable of suppressing, delaying, ameliorating, treating or alleviating cardiovascular disease and/or osteoporosis. Those skilled in the art should be aware that the effective amount may vary from one individual to another depending on factors such as age, etc.

In the present disclosure, the 'mixed extract' refers to a mixture of two or more plant extracts, and may contain a mixture of two, three, four or more plant extracts. The mixed extract may be obtained by mixing two or more plant extracts or by mixing two or more plants and extracting the mixture. The mixed extract may be provided into various ingestible forms, specifically a dry powder.

The content of the mixed extract contained in the composition is not specially limited. The mixed extract may be contained in various amounts as long as it can prevent, alleviate or treat cardiovascular disease and/or osteoporosis. For example, the mixed extract of hop and *Cynanchum wilfordii* may be contained in an amount of 0.01-65 wt %, 0.1-60 wt %, 1-55 wt %, 10-52 wt %, 15-51 wt % or 20-50 wt % based on the total composition. In another exemplary embodiment, the mixed extract may contain a mixture of a hop extract and a *Cynanchum wilfordii* extract at a weight ratio of 1:0.1-10, specifically 1:0.15-8, more specifically 1:0.5-5, further more specifically 1:1-3. When the extracts are mixed within the above ranges, the effect of alleviating cardiovascular disease and/or osteoporosis may be superior. In addition, the astringent taste of hop may be reduced and preference may be improved.

In an exemplary embodiment of the present disclosure, the extract may be contained in an amount of 1-1000 mg, specifically 5-500 mg, based on 1 g of the composition. Specifically, the contents of all the ingredients used in the present disclosure do not exceed the maximum contents stated in the related laws and regulations of Korea, China, the Unites States, Europe, Japan, etc. (e.g., Regulations on the Safety Standards, etc. of Cosmetics (Korea), Safety and Technical Standards for Cosmetics (China), Food Code (Korea), Food Additives Code (Korea), Health Functional Food Code (Korea), Hygiene Standers (China), etc.). That is to say, the ingredients according to the present disclosure are contained in the cosmetic, food or personal care composition according to the present disclosure within the content limits permitted by the related laws, regulations and standards of each country.

In the present disclosure, the 'extract' may be prepared by extracting a plant, etc. with an extraction solvent or by conducting fractionation by adding a fractionation solvent to an extract prepared by extracting with the extraction solvent. The extract may be extracted by various methods such as hot water extraction, distillation extraction, solvent extraction, compression extraction, cold extraction, reflux cooling extraction, ultrasonic extraction, electrolytic extraction, supercritical extraction, etc., and may also be extracted using two or more extraction methods described above. A fraction obtained by fractionating the mixed extract of the present disclosure may also be included in the scope of the present disclosure.

The extract or fraction includes the extract itself and all forms of extracts that can be obtained from the extract, including a dried product obtained by diluting or concentrating the extract and then drying the same, a crude product or purified product of the extract, a mixture thereof, etc. Specifically, the extract of the present disclosure may be prepared into a dry powder after extraction. In addition, after performing extraction or fractionation, the extract may be concentrated or the solvent may be removed by filtration under reduced pressure and additional concentration and/or freeze-drying. The obtained extract may be stored in a deep freezer until use.

The extraction solvent is not specially limited and any solvent known in the art may be used as long as the extract exhibiting the effect desired by the present disclosure can be achieved. Specifically, one or more selected from a group consisting of water and an organic solvent may be used. One or more solvent selected from a group consisting of a $C_{1-5}$ alcohol such as methanol, ethanol, etc., ethyl acetate, acetone and chloroform may be used as the organic solvent. Specifically, water, ethanol or a mixture thereof may be used. Specifically, 35-95% ethanol, more specifically 60-90% ethanol, may be used as the ethanol.

In addition, the term 'extract' used in the present specification means a crude extract in the art as described above but also includes a fraction obtained by additionally fractionating the extract in a broad sense. That is to say, it includes not only an extract obtained by squeezing or extracting a raw material with the extraction solvent described above but also a product obtained by further purifying the same. For example, a fraction obtained by passing the extract through an ultrafiltration membrane having a certain molecular weight cut-off value and fractions obtained by various additional purification methods such as chromatography (designed for separation according to size, charge, hydrophobicity or affinity) are included in the extract of the present disclosure.

In addition, the mixed extract of the present disclosure may pass through an additional process, e.g., removal of the solvent through filtration, concentration or drying, or all of filtration, concentration and drying. For example, the filtration may be performed using filter paper or a vacuum filter, the concentration may be performed using a vacuum concentrator, and the drying may be performed by spray drying, freeze-drying, etc. to obtain the mixed extract in the form of a powder.

In the mixed extract of the present disclosure, the hop extract may be obtained by extracting hop with ethanol after supercritical extraction and then preparing the same into a powder and may be purchased, for example, from Naturex (France). The *Cynanchum wilfordii* extract may be obtained by extracting *Cynanchum wilfordii* with hot water and then preparing the same into a powder. Specifically, in a method for preparing the mixed extract according to an exemplary embodiment of the present disclosure, the extraction method may not be specially limited as long as the hop extract can contain 0.1-8 mg, specifically 0.5-5 mg, more specifically 1-4 mg, of 8-prenylnaringenin per 1 g of the extract. In addition, the extraction method may not be specially limited as long as the *Cynanchum wilfordii* extract can contain 0.1-3 mg, specifically 0.15-1 mg, more specifically 0.2-0.5 mg, of caudatin per 1 g of the extract.

When extracted by the extraction method described above, the mixed extract may exhibit superior effect of treating osteoporosis or cardiovascular disease.

In an exemplary embodiment of the present disclosure, the composition may contain 0.1-5 mg, specifically 0.5-3 mg, more specifically 0.6-1.50 mg, of 8-prenylnaringenin, which is a marker compound of the hop extract, based on 1 g of the composition containing the mixed extract. In addition, the mixed extract may contain 0.05-1.5 mg, specifically 0.1-1 mg, more specifically 0.15-0.5 mg, further more specifically 0.16-0.3 mg, of caudatin, which is a marker compound of the *Cynanchum wilfordii* extract, based on 1 g of the composition containing the mixed extract. The above content ranges may be advantageous for achieving the purpose of the present disclosure. In a specific example, when the degree of alleviation of cardiovascular disease and/or osteoporosis was investigated using the mixed extract, it was confirmed that cholesterol synthase was inhibited and the production of bone tissue components was excellent in a test group which ingested the mixed extract of the present disclosure. In particular, the composition of the present disclosure may exhibit excellent effect of reducing blood cholesterol level and inhibiting osteoclast differentiation.

In another exemplary embodiment, the fractionation solvent may be water, butanol, ethyl acetate, chloroform, hexane or a mixture thereof. The fraction may be obtained by fractionating an extract, specifically a crude extract, prepared by the extraction method described above. The fractionation solvent may be a solvent selected from a group consisting of ethyl acetate, ether, chloroform, benzene, hexane, methylene chloride and a mixed solvent thereof. Specifically, it may be hexane. Specifically, the fractionation may be performed by sequentially adding hexane, chloroform, ethyl acetate, butanol and water to a crude extract and then sequentially obtaining a hexane fraction, a chloroform fraction, an ethyl acetate fraction, a butanol fraction and a water fraction.

In the present disclosure, the method for preparing the extract or the mixed extract is not limited specially and methods commonly used in the art may be employed. Non-limiting examples of the extraction method include hot water extraction, ultrasonic extraction, filtration, reflux extraction, etc., and these may be performed alone or in combination. In addition, the extract may be extracted further one or more times in the same manner to obtain a high-purity extract.

The present disclosure may provide a composition for preventing or alleviating cardiovascular disease and/or osteoporosis, which contains the mixed extract as an active ingredient. Specifically, the composition may be provided in the form of pharmaceuticals, foods or quasi-drugs. Particularly, it may be provided as specifically a health functional food or a medicine.

The pharmaceutical composition according to the present disclosure may contain a pharmaceutically effective amount of the mixed extract either alone or in combination with one or more pharmaceutically acceptable carrier or additive. The "pharmaceutically acceptable" means that the composition is physiologically acceptable and nontoxic when administered to human, without inhibiting the action of the active ingredient or causing allergic reactions such as gastrointestinal disorders and dizziness or similar reactions. The type of the carrier that may be used in the present disclosure is not specially limited, and any pharmaceutically acceptable carrier commonly used in the art may be used. Non-limiting examples of the carrier include saline, sterile water, Ringer's solution, buffered saline, albumin injection solution, dextrose solution, maltodextrin solution, glycerol, ethanol, etc. These may be used either alone or in combination. Examples of the additive include lactose, dextrose, sucrose, sorbitol, mannitol, xylitol, erythritol, maltitol, starch, acacia gum, alginate, gelatin, calcium phosphate, calcium silicate, cellulose, methyl cellulose, polyvinylpyrrolidone, methyl hydroxybenzoate, propyl hydroxybenzoate, talc, magnesium stearate, mineral oil, etc. In addition, the pharmaceutical composition may further contain a filler, an anti-coagulant, a lubricant, a wetting agent, a flavoring agent, an emulsifier, an antiseptic, etc.

The "pharmaceutically effective amount" refers to an amount which exhibits a greater response than that of a negative control group, and specifically refers to an amount which is sufficient to exhibit the effect of preventing, alleviating and/or treating cardiovascular disease and/or osteoporosis.

In addition, the pharmaceutical composition of the present disclosure may be formulated by a method known in the art to provide rapid, sustained or delayed release of the active ingredient after administration to a mammal. The formulation may be in the form of a powder, a granule, a tablet, an emulsion, a syrup, an aerosol, a soft or hard gelatin capsule, a sterilized injectable solution or a sterile powder.

The pharmaceutical composition of the present disclosure may be administered orally or parenterally although the administration route is not limited thereto. The parenteral administration route may include various routes such as transdermal, intranasal, intraperitoneal, intramuscular, subcutaneous or intravenous routes.

In addition, the pharmaceutical composition of the present disclosure may be administered with in combination with a known compound having the effect of preventing, alleviating and/or treating cardiovascular disease and/or osteoporosis.

In another exemplary embodiment, the present disclosure provides a food composition.

The food composition of the present disclosure includes all processed forms of natural materials such as a food, a functional food, a nutritional supplement, a health food, a food additive, etc. The food composition can be prepared into various forms according to common methods known in the art. For example, as a health food, the composition of the present disclosure itself may be prepared into a tea, a juice or a drink for drinking, or may be granulated, encapsulated or powdered for ingestion.

The type of the food is not specially limited and may include any food in the conventional sense. Non-limiting examples of the food to which the composition can be added include meat, sausage, bread, chocolate, candy, snack, confectionery, pizza, ramen, other noodles, gum, dairy products including ice cream, soup, beverages, tea, drinks, alcoholic beverages, vitamin complexes, etc. When the composition is used as a food additive, the composition may be added as it is or may be used together with other foods or food ingredients, and may be used appropriately according to common methods. In addition, the food composition of the present disclosure may further contain another active ingredient and/or additive that can be commonly used in a food composition. The food composition may contain a sitologically acceptable carrier. For example, the food composition according to the present disclosure may contain water-soluble vitamins such as thiamine (vitamin $B_1$), riboflavin, ascorbic acid, niacin and vitamin B6, fatty acids such as myristic acid, palmitic acid, stearic acid, oleic acid, linoleic acid, etc., a weak acid such as glycolic acid and acetic acid, and amino acids such as 8 essential amino acids, threonine, valine, methionine, isoleucine, leucine, phenylalanine, tryptophan and lysine, and aspartic acid, serine, glutamic acid, proline, glycine, alanine, cysteine, tyrosine, histidine, arginine, etc.

Specifically, the food composition of the present disclosure may be obtained by mixing the mixed extract with crystalline cellulose, lactose, seaweed powder, hydroxypropylmethyl cellulose, crosslinked sodium carboxymethyl cellulose, silicon dioxide, magnesium stearate, etc.

In another exemplary embodiment, the present disclosure provides a method for preventing or treating osteoporosis and/or cardiovascular disease, which includes a step of administering an effective amount of the mixed extract or a composition containing the mixed extract to an individual who suffers from or has the risk of osteoporosis and/or cardiovascular disease. In the present disclosure, the term "individual" refers to all animals including human, such as rat, mouse, livestock, etc., that suffer from or have the risk of osteoporosis and/or cardiovascular disease. As a specific example, it may be a mammal including human. The composition of the present disclosure may be administered with a daily dose of 0.0001-100 mg/body weight kg, more specifically 0.001-100 mg/body weight kg, based on solid content. The recommended administration dose may be administered once a day or in several divided doses.

In another exemplary embodiment, the present disclosure provides a method for treating or alleviating cardiovascular disease and/or osteoporosis by administering an effective amount of a mixed extract of hop and *Cynanchum wilfordii* to an individual in need of treatment or alleviation of cardiovascular disease and/or osteoporosis.

The mixed extract may be a mixture of a hop extract and a *Cynanchum wilfordii* extract at a weight ratio of 1:0.1-10.

The method may include a step of administering a composition containing the mixed extract, and the composition may contain 8-15 wt % of a hop extract and 20-30 wt % of a *Cynanchum wilfordii* extract based on the total weight of the composition.

The mixed extract used in the method for alleviation or treatment contains 8-prenylnaringenin and hesperidin. The mixed extract may contain 0.1-8 mg/g of 8-prenylnaringenin and 0.05-1.5 mg/g of caudatin.

The method may provide reduction of blood cholesterol concentration and osteoclast differentiation inhibition.

In another exemplary embodiment, the present disclosure provides a use of the composition containing the mixed extract for preparation of a food or a therapeutic agent for alleviating, treating, preventing or ameliorating cardiovascular disease and/or osteoporosis.

Hereinafter, examples, etc. will be described in detail to held understanding the present disclosure. However, the examples according to the present disclosure may be changed into various different forms, and the scope of the present disclosure should not be construed as being limited by the examples. The examples of the present disclosure are provided to more completely explain the present disclosure to those having ordinary knowledge in the art to which the present disclosure belongs. In the present specification, % may be understood to mean wt % unless specified otherwise.

<Preparation of Mixed Extract>

1. Preparation of Hop Extract

Hop was extracted using the flower of *Humulus lupulus* L by supercritical and ethanol extraction. Then, the extract was pulverized after passing through concentration, alkalinization, neutralization, separation and drying.

A hop extract containing 2-3 mg/g of 8-prenylnaringenin was prepared.

2. Preparation of *Cynanchum wilfordii* Extract

*Cynanchum wilfordii* was extracted using the tuberous root of *Cynanchum wilfordii* by hot water extraction. Then, the extract was pulverized after passing through filtration, concentration and drying.

A *Cynanchum wilfordii* extract containing 0.26-0.39 mg/g of caudatin was prepared.

3. Preparation of Mixed Extract

A mixed extract was prepared by mixing the natural extracts.

<Confirmation of Synergistic Effect>

It was confirmed that the treatment with a mixed extract of hop and *Cynanchum wilfordii* had statistically significant effect (synergistic effect) of increasing the inhibition of cholesterol synthase, promoting NO production, promoting osteoblast differentiation and producing bone tissue components as compared to when the hop extract or the *Cynanchum wilfordii* extract was treated alone. The interaction between the two extracts was confirmed by the method of Colby (Colby S. R., Calculating synergistic and antagonistic response of herbicide combinations, Weeds 15, 20-22, 1967), which is one of the methods for confirming the synergistic effect of a mixture described in the Guideline for Standardization of Functional ingredients of the Korea Food and Drug Administration. It is judged that there is synergistic effect when the actual value observed after treating with the mixed extract is greater than the expected value (as calculated by Equation 1).

$$E=(X+Y)-XY/100 \qquad \text{[Equation 1]}$$

X is the effect of the treatment with an active ingredient A (or extract A) with respect to an untreated control group, Y is the effect of the treatment with an active ingredient B (or extract B) with respect to an untreated control group, and E is the effect (%) of the treatment with active ingredients A and B (or extract A and extract B) with respect to an untreated control group. It can be seen that there is synergistic effect if the observed value exceeds E.

In the Experimental examples described below, the mixed extract exhibited synergistic effect over the individual extracts with the measurement values exceeding the expected values.

Experimental Example 1. Evaluation of Osteoblast Differentiation-Promoting Effect In order to investigate osteoblast differentiation-promoting effect, the activity of ALP (alkaline phosphatase), which is an osteoblast differentiation marker, in human osteoblast-like Saos-2 cells was measured. A uniform number of Saos-2 cells were cultured in a 24-well plate using a RPMI1640 medium supplemented with 10% FBS. After culturing for 24 hours, the medium was replaced with a phenol red-free RPMI1640 containing 2% charcoal-stripped FBS and the cells were cultured further for 3 days after treating with samples at different concentrations. Subsequently, ALP activity was measured with an alkaline phosphatase assay kit (Abcam, ab83369). Specifically, 200 μL of the cell culture was collected and centrifuged at 1000 rpm for 3 minutes. After putting 20 μL of the medium in the upper layer and 50 μL of a pNPP substrate into a 96-well plate and conducting reaction for 30 minutes, absorbance was measured at 405 nm. The result is shown in Table 1. It can be seen that when the mixed extract was used, the differentiation into osteoblasts was facilitated as compared to when the hop was used alone.

Experimental Example 2. Evaluation of Bone Component (Osteocalcin) Production-Promoting Effect In order to investigate osteogenesis-promoting effect, a uniform number of Saos-2 cells were cultured in a 24-well plate using a RPMI1640 medium supplemented with 10% FBS. After culturing for 24 hours, the medium was replaced with a phenol red-free RPMI1640 containing 10 mM β-glycerophosphate, 10 nM dexamethasone and 2% charcoal-stripped FBS and the cells were cultured further for 3 days after treating with samples at different concentrations. Subsequently, after changing the medium and treating with the samples in the same way, the cells were cultured further for 4 days. After culturing for a total of 7 days, 200 μL of the cell culture was collected and centrifuged at 1000 rpm for 3 minutes. Osteocalcin in the medium in the upper layer was quantified using a human osteocalcin DuoSet ELISA kit (R&D Systems, DY1419) according to the manufacturer's protocol. The result is shown in Table 1. It can be seen that when the mixed extract was used, the bone component production was facilitated as compared to when the hop was used alone.

Experimental Example 3. Evaluation of Inhibition of Cholesterol Synthase HMG-CoA Reductase Activity The effect of inhibiting the activity of HMG-CoA reductase, which is a rate-limiting enzyme in cholesterol synthesis, was investigated using an HMG-CoA reductase activity assay kit (Abcam, AB204701). The activity of HMG-CoA reductase was measured according to the manufacturer's protocol. The result is shown in Table 1. It can be seen that when the mixed extract was used, the activity of the cholesterol synthase was inhibited more than when the hop was used alone. Through this, it can be seen that the mixed extract has excellent effect of improving blood lipids.

Experimental Example 4. Evaluation of Promotion of Production of Blood Vessel-Relaxing Nitric Oxide (NO)

Nitric oxide (NO) is a signaling molecule involved in various physiological activities such as immunity, vasodilation, signaling, etc. In particular, it induces and stimulates various activities in the body. It dilates blood vessels and lowers blood pressure to a normal level by inducing the production of cGMP (cyclic guanosine monophosphate) and improves the flow of blood supplied to organs. In addition, it is effective in preventing stroke and, especially, heart attack such as myocardial infarction, etc. by preventing blood clots from adhering to blood vessels in the cardiovascular system.

In order to investigate the NO production-promoting effect of the samples, human umbilical vein endothelial cells (HUVECs) were inoculated to a 24-well plate (Falcon, 353047) with $1 \times 10^5$ cells per well and cultured for 24 hours using an EGM-2 medium (Lonza, CC-3162 containing an appropriate amount of FBS (fetal bovine serum) and P/S antibiotics (penicillin and streptomycin) under the condition of 5% $CO_2$ and 37° C., until about 80% more of the cells were adhered to the bottom of the well. Subsequently, after treating with the sample of each concentration, the cells were cultured further for 24 hours. After the culturing was completed, the concentration of NO in the medium was measured using a Griess reagent (Sigma, G4410). Specifically, 100 μL of the medium was mixed with 100 μL of the Griess reagent and measurement was made at a wavelength of 540 nm using a UV spectrophotometer (Biotek, Synergy H1MF). The result is shown in Table 1. It can be seen that when the mixed extract was used, the production of NO was increased as compared to when the hop was used alone. Through this, it can be seen that the mixed extract has excellent effect of improving blood flow by dilating blood vessels and preventing stroke and, especially, heart attack such as myocardial infarction, etc. by preventing blood clotting in the cardiovascular system.

The results of the Experimental Examples 1~4 are summarized in the following table. The results are expressed as % improvement with respect to an untreated control group.

TABLE 1

| Samples | Conc. | Cardiovascular markers | | Osteoporosis markers | |
| | | Inhibition of cholesterol synthase activity (%) | Promotion of production of blood vessel-relaxing NO (%) | Promotion o of differentiation of osteoblasts (%) | Production of bone tissue components (%) |
|---|---|---|---|---|---|
| Hop | 5 ppm | 17.80 | 16.35 | 12.52 | 11.99 |
| | 10 ppm | 18.11 | 19.11 | 13.64 | 13.10 |
| Cynanchum wilfordii | 5 ppm | 12.26 | 12.01 | 17.71 | 16.29 |
| | 10 ppm | 14.23 | 14.87 | 18.18 | 19.47 |
| Hop + Cynanchum wilfordii (mixture of hop:Cynanchum wilfordii at a weight ratio 1:2) | 5 ppm | 42.04 | 43.49 | 38.96 | 40.03 |
| | 10 ppm | 44.27 | 45.48 | 43.39 | 42.73 |

(n = 3)

<In-Vivo Experiment>

Additional experiment was conducted as follows to investigate blood cholesterol-improving effect and osteoclast differentiation-inhibiting effect.

In-Vivo Experiment on Blood Cholesterol-Improving Effect 7-week-old ICR mice purchased form Dae Han Biolink (Eumseong, Chungbuk) were accustomed for a week. After conducting ovariotomy, the mice were orally administered with samples for 7 weeks from one week after the ovariotomy. Total cholesterol level in blood was measured using DRI-CHEM NX-500i (Fujifilm) before the administration and at 7 weeks after the administration.

In-Vivo Experiment on Osteoclast Differentiation-Inhibiting Effect 7-week-old ICR mice purchased form Dae Han Biolink (Eumseong, Chungbuk) were accustomed for a week. After conducting ovariotomy, the mice were orally administered with samples for 7 weeks from one week after the ovariotomy. The level of tartrate-resistant acid phosphatase (TRACP) in serum was measured using a TRACP ELISA kit (MyBioSource) according to the manufacturer's protocol before and after the administration.

TABLE 2

| Test groups | Daily intake (mg/kg) | Cardiovascular disease Improvement of blood cholesterol (%) | Osteoporosis Inhibition of osteoclast differentiation (%) |
|---|---|---|---|
| Hop | 60 | 23.4 | 11.0 |
| Cynanchum wilfordii | 120 | 21.2 | 9.8 |
| Hop + Cynanchum wilfordii | 20 + 40 | 50.0 | 21.5 |
| Hop + Cynanchum wilfordii (Colby's E value) | 60 + 120 | 39.6 | 19.7 |

The mixed extract of Cynanchum wilfordii and hop showed higher improvement even with a smaller amount. In particular, it exhibited excellent effect of alleviating cardiovascular disease and osteoporosis even though the amount of hop was reduced. Accordingly, a composition that can be ingested safely with no side effect can be provided.

<Sensory Evaluation>

Sensory evaluation was conducted by 20 trained subjects. They were asked to ingest the powders prepared according to the mixing ratios shown in Table 3 at a dose of 500 mg per each intake. The evaluation items consisted of a total of four items: 1) bitter taste felt immediately after the intake, 2) bitter aftertaste felt 5 minutes after the intake, 3) preference for flavor felt during the intake, and 4) overall preference. Each item was evaluated on a 9-point scale. For the bitter taste and the bitter aftertaste, a higher score means stronger bitterness. For the flavor and overall preference, a higher score means higher preference. The result is shown in Table 4.

TABLE 3

| | Samples | Mixing ratio (%) | |
| | | Comparative Example | Example |
|---|---|---|---|
| | Hop | 36 | 12 |
| | Cynanchum wilfordii | — | 24 |
| Food additives | Crystalline cellulose | 18 | |
| | Lactose | 20 | |
| | Seaweed powder | 20 | |
| | HPMC | 1 | |
| | Crosslinked CMC-Na | 3 | |
| | Silicon dioxide | 1 | |
| | Magnesium stearate | 1 | |

For the example, a powder of a hop extract and a powder of a Cynanchum wilfordii extract were mixed, and then the food additives described above were mixed.

TABLE 4

| Test groups | Sensory scores | | | |
| | Bitter taste | Bitter aftertaste | Preference for flavor | Overall preference |
|---|---|---|---|---|
| Hop (Comparative Example) | 7.9 | 7.1 | 3.8 | 2.1 |
| Hop + Cynanchum wilfordii (Example) | 5.2 | 4.8 | 5.5 | 5.4 |

When the hop was used alone, the bitter taste was strong and the preference was low.

When the mixed extract of hop and Cynanchum wilfordii was used, the preference for taste and flavor was increased in addition to superior effect as compared to when the hop was used alone.

What is claimed is:

1. A method for treating or alleviating cardiovascular disease and/or osteoporosis, comprising:

a step of administering an effective amount of a mixed extract of hop and Cynanchum wilfordii to an individual in need of treatment or alleviation of cardiovascular disease and/or osteoporosis, wherein the mixed extract is a mixture of a hop extract and a Cynanchum wilfordii extract at a weight ratio of 1:2.

2. The method for treating or alleviating cardiovascular disease and/or osteoporosis according to claim 1, wherein the method comprises a step of administering a composition comprising the mixed extract, and the composition comprises 8-15 wt % of a hop extract and 20-30 wt % of a *Cynanchum wilfordii* extract based on the total weight of the composition.

3. The method for treating or alleviating cardiovascular disease and/or osteoporosis according to claim 1, wherein the mixed extract comprises 8-prenylnaringenin and caudatin, and the mixed extract comprises 2-3 mg/g of 8-prenylnaringenin and 0.26-0.39 mg/g of caudatin.

4. The method for treating or alleviating cardiovascular disease and/or osteoporosis according to claim 1, wherein the method provides reduction of blood cholesterol concentration and osteoclast differentiation inhibition.

5. The method for treating or alleviating cardiovascular disease and/or osteoporosis according to claim 1, wherein the method treats or alleviates cardiovascular disease and osteoporosis.

* * * * *